(12) United States Patent
Silber et al.

(10) Patent No.: US 8,624,053 B2
(45) Date of Patent: Jan. 7, 2014

(54) METHOD TO PRODUCE A STABLE DRY IONIC-BONDED CREATINE α KETOGLUTARATE OF HIGH ORAL ABSORBABILITY

(71) Applicants: Moris Silber, Baltimore, MD (US); Timur Yusufov, Pikesville, MD (US)

(72) Inventors: Moris Silber, Baltimore, MD (US); Timur Yusufov, Pikesville, MD (US)

( * ) Notice: Subject to any disclaimer, the term of this patent is extended or adjusted under 35 U.S.C. 154(b) by 0 days.

(21) Appl. No.: 13/744,240

(22) Filed: Jan. 17, 2013

(65) Prior Publication Data
US 2013/0184487 A1    Jul. 18, 2013

Related U.S. Application Data

(60) Provisional application No. 61/587,335, filed on Jan. 17, 2012.

(51) Int. Cl.
*C07C 271/22* (2006.01)

(52) U.S. Cl.
USPC .................. 560/158; 204/157.6; 204/157.63; 204/156

(58) Field of Classification Search
USPC .......................... 560/158; 204/157.6, 157.63
See application file for complete search history.

(56) References Cited

U.S. PATENT DOCUMENTS

2008/0103202 A1* 5/2008 Ferguson et al. ............. 514/551

* cited by examiner

*Primary Examiner* — Yong Chu
(74) *Attorney, Agent, or Firm* — Michael David

(57) ABSTRACT

The invention provides a method to produce a stable, ionic-bonded, dry creatine-α-ketoglutarate product at a molar ratio of about 2:1. The product is stable at room temperature when kept dry for periods of up to one year. The product can be supplemented with additional biologically active, natural amino acid, preferably l-arginine, l-taurine and l-citrulline. The serving dosage is typically between about 1 and 2 g.

21 Claims, 4 Drawing Sheets

METHOD TO PRODUCE A STABLE DRY IONIC-BONDED CREATINE α KETOGLUTARATE OF HIGH ORAL ABSORBABILITY

This application claims priority from U.S. Provisional Application 61/587,335 filed Jan. 17, 2012. The provisional application, in its entirety, is incorporated in the present application, by reference.

BACKGROUND OF THE INVENTION

1. Field of the Invention

This invention relates to the field of nutritional supplements and in particular to a chemical composition comprising a stable dry ionic-bonded product bio-engineered from creatine monohydrate and α-ketoglutarate.

2. Description of the Background

Creatine (Cr) is an amino acid derivative (α-methyl guanidine-acetic acid) naturally present in the human body. It is either taken up from food by intestinal absorption or is synthesized endogenously, primarily in kidney, pancreas, and liver. See: creatine and creatine Deficiency Syndromes. 2010 by Elsevier: 163-171. There is a marked separation between the tissues that produce creatine and those that utilize most of it. creatine is distributed throughout the body, 95% found in skeletal muscle, and most of the remaining 5% of the creatine pool is located in brain, liver, kidney, and testis. Brain has an autonomous creatine synthesis pathway, the blood-brain barrier being poorly permeable to creatine. See: Functions and Effects of creatine in the Central Nervous System. 2008 Brain Res Bull; 76: 329-43. Thus the liver-kidney axis for endogenous creatine synthesis is apparently essential for providing creatine to peripheral tissues (including muscle), but to a lesser extend for the brain. A Na+-driven plasma membrane creatine transporter in brain, muscle, heart, and kidney is required for cellular uptake of creatine. See: Extracellular creatine regulates creatine transport in rat and human muscle cells. 1988 Proc. Natl. Acad. Sci USA; 85: 807-11. Circulating creatine is taken up into creatine-requiring tissues by creatine-transporter, which spans the plasma membrane, against a large concentration gradient: plasma [Cr] 50 µmol/L against intracellular [Cr+CP]>40 mmol/L. See: creatine and the creatine transporter: a review 2001. Mol. Cell Biochem; 224: 169-81.

In the cell, creatine is part of the creatine Kinase (CK) system that provides for the Adenosine tri-phosphate (ATP) re-synthesis, which is a key energy source for every metabolic activity. Disturbances of the CK system have been reported in muscle, brain, cardiac and renal malfunctions. On the other hand, creatine was found to have ergogenic, antitumor, antiviral, and anti-diabetic effects and to protect tissues from hypoxic, ischemic, neurodegenerative, and muscle damage. See: Creatine and Creatinine Metabolism 2000 July; 80 (3): 1107-213. Oral creatine ingestion is popular with athletes who wish to build up muscle, as well as with aging subjects to slow down muscle loss.

The estimated total body pool of total Cr in a 158 Lbs (70 kg) man is about 120 g (See: Elevation of creatine in resting and exercised muscle of normal subjects by creatine supplementation 1992. Clin. Sci; 83: 367-74). Based on measurements of renal excretion of creatinine (Crn), the daily requirement for Cr from endogenous biosynthesis, is approximately 2 g/day, or 340 µmol/kg/day. This suggests a relatively slow turnover rate of creatine in skeletal muscle with a $T_{1/2}$ of approximately 26 days (See: Scientific facts behind creatine monohydrate as sport nutrition supplement 1999. J. Sports Med. Phys. Fitness; 39 (3): 179-88).

Given these circumstances, there is an important need in the art for a method to improve the absorption of creatine along with its further expedient delivery to the target tissue and inside the cells. This would allow inter-alia a better control over the dosage/effect dependence for creatine supplementation and overly improve its quality. Previous attempts have focused on improving the digestive absorbability of creatine by enhancing its solubility, but these earlier attempts did not create the desired increased absorbability. See: creatine: 12 Facts Every Consumer Should Know 2005, AAEFX.

α-Ketoglutarate is also a natural compound synthesized in a mammal as part of the Krebs cycle. It has high chemical affinity for nitrogen to reduce nitrogen overload and also for trans-amination, and plays a role in the prevention of ammonia toxicity. As an important intermediate in the Krebs cycle, α-ketoglutarate easily permeates muscle cell membrane and α-ketoglutarate has been a desirable tool to boost muscle energy. Furthermore, α-ketoglutarate is a co-catalyst by undergoing oxygenation alongside oxygenases, to permit oxygenation of various cellular targets. It is often a compound recommended to athletes. In contrast, in the present invention, α-ketoglutarate is utilized because of its remarkably high chemical affinity for nitrogen in general, but, particularly, for the guanidine-functional group from creatine. As described below, we were able to exploit this property of α-ketoglutarate in bioengineering an ionic-bonded creatine α-ketoglutarate vehicle for creatine to deliver the latter to the muscle against a pre-existing high concentration gradient barrier for dietary creatine.

Each of l-Arginine, l-Taurine, and l-Citrulline are often provided for enhancing muscle strength and mass. See: Citrulline/malate promotes aerobic energy production in human exercising muscle 2002. Br J. Sports Med. 36(4):282-9, PMID 12145119. All three are semi-essential or non-essential amino acids formed naturally in the body. L-Arginine is the universal precursor for endogenous creatine and nitric oxide (NO) biosynthesis. See: Argenine: Clinical potential of a semi-essential amino 2002. Altern. Med. Rev. December; 7(6): 512-22. L-Taurine is ultimate sulfur donator for the cystein-cystine redox (antioxidant) system, alongside with glutothione. L-Citrulline, like l-arginine and l-ornithine is a metabolite in the urea cycle and is involved in liver detoxification and vasodilation pathways. Formed from glutamic acid and ornithine in the body, it is added by others to many formulas in an attempt to spare l-arginine for production of NO. See: Citrullin/malate promotes aerobic energy production in human exercising muscle 2002. Br. J. Sports Med. August; 36(4): 282-9. Yet, there is a dramatic difference in the doses of these amino acids used elsewhere, compared to both the dosage and the role of creatine as a bioavailability enhancing factor.

SUMMARY OF THE INVENTION

The invention provides a method of preparing a dry, non-oxidized, stable complex of creatine and α-ketoglutarate product with enhanced stability and absorbability. The method comprises:

in a thermo-stable reactor, provide in powder form, creatine monohydrate and

α-ketoglutarate and a compound to allow the adjusting and maintaining the pH at between about 5.8 to 7 (together a mixture); stir and blend; and provide electromagnetic energy to achieve an internal temperature of about 61° C. for a period of time sufficient to allow an ionic-bonding of the creatine and alpha-ketoglutarate, whereas the product is at a molar ratio of 2:1 of creatine:alpha-ketoglutarate, and the product is dry, non-oxidized and stable.

In a preferred embodiment, the step to provide electromagnetic energy optionally comprises cycles of short bursts of energy followed by short cooling periods.
1. In yet other preferred embodiment the creatine and alpha-ketoglutarate ingredients are provided at a ratio of from about 2 to 2.4 moles of creatine monohydrate to about 1 mole of alpha-ketoglutaric acid. More preferably, yet the creatine monohydrate and alpha-ketoglutaric acid ingredients are provided at a molar ratio of about 2.25:1.

In another preferred embodiment, the cooling is accompanied by blending the ingredients to allow more rapid cooling and to release water vapors from the mixture.

In still another preferred embodiment, the compound added to control the pH is calcium carbonate, at between about 0.2 M and about 0.6 M. Preferably, the pH is maintained at about 6.8.

In accordance to another embodiment, the products after the bonding process is finished are fine milled. Preferably, the products, while undergoing milling, are maintained at a temperature of between 41° C. and 61° C.

In one preferred embodiment, after the milling, the powder product is exposed to an electrical field creating an accumulation of unreacted ionic or cationic compounds at the positive and negative electrode, respectively, and the material accumulated at the poles is removed away from the end product remaining in the mixing reactor, wherein the remaining product comprises stably conjugated creatine and α-ketoglutarate. Preferably, the creatine α-ketoglutarate product, after the removal of unreacted compounds, the creatine is present to at least about 55%, 65%, 70%, 75%, 80%, 85%, 90%, or 95% as an ionic-bonded product with α-ketoglutarate.

In a preferred embodiment, the product further contains at least one from among l-arginine; l-taurine; and citrulline, which are added and blended with the creatine-α-ketoglutarate conjugate.

In a preferred embodiment, the amount of starting ingredients may comprises about 40-45 grams creatine monohydrate; about 20 grams α-ketoglutarate; from about 2 to about 6 grams calcium carbonate, about 15 grams of l-arginine; about 15 grams of l-taurine; and about 1.5 grams of citrulline. Preferably, the amount of calcium carbonate is about 5 grams. The method may be scaled up from the amounts presented above. That requires that the relative ratio of the ingredients is preserved and the electromagnetic energy is adjusted to achieve the ionic bonding.

The resulting creatine and α-ketoglutarate product is preferentially stored in a reduced humidity environment until ingestion by a patient, preferably in a kit form of individual doses. The kid optionally provides instructions for oral cavity ingestion of the product, as opposed to swallowing the powders.

The invention also provides a creatine α-ketoglutarate product made by the method of the invention.

DETAILED DESCRIPTION

The invention consists of the application of bio-engineering technology comprising generation of a series of intermittent electromagnetic discharges from a medium power benchtop magnetron device to yield an ion-bonded creatine α-ketoglutarate product of high biological activity, as estimated by athletic performance tests. Magnetron discharge creates weakly ionized plasma that can affect organic molecules. There are several effects associated with magnetron plasma: electrons having temperature of about 2-3 eV (20,000-30,000 K) and energetic ions.

The invention provides a method of preparing a conjugate of creatine and α-ketoglutarate, which is stable-at-room-temperature. The product is created in a reaction between the ingredients in the absence of solvents; indeed it is a reaction of essentially dry powder ingredients. A dry, uniformly micronized fine powder creatine α-ketoglutarate ioinic bonded product is created. The method is carried out in a manner that reduces the potential oxidation of the product. The dry product, preferably stored under desiccating conditions, is stable at temperatures ranging from about 18° C. to 22° C. for extended periods of time, up to about one year.

The complex of creatine and α-ketoglutarate is effective as a skeletal muscle protein biosynthesis booster and torque energy regenerator for periods of up to at least about 6 months, and typically for longer periods, up to about 1 year. These attributes render the creatine α-ketoglutarate product highly efficient as an athletic performance enhancer and a health improving supplement. Its delivery to the target tissue is faster and bioavailability higher.

Albeit the invention is not limited by any specific chemical interactions between the ingredients that renders the creatine and α-ketoglutarate into a stable composition, it is believed that the product is rendered stable provided by strong ionic interaction (ionic bonding).

The starting ingredients are also referred to as creatine monohydrate and α-ketoglutaric acid.

Herein the term "stable" has two meanings, depending on the context: it refers to the general stability of the product for increased lengths of time as shown by its ability to deliver increased performance after storage; it also refers to the ability to show the product as a new peak after analysis of freshly made product or stored product after the mechanical and chemical manipulation involved in the analysis of the Product, e.g., by HPLC-MS and UV-absorption studies or by NIR analysis.

Figure 1:
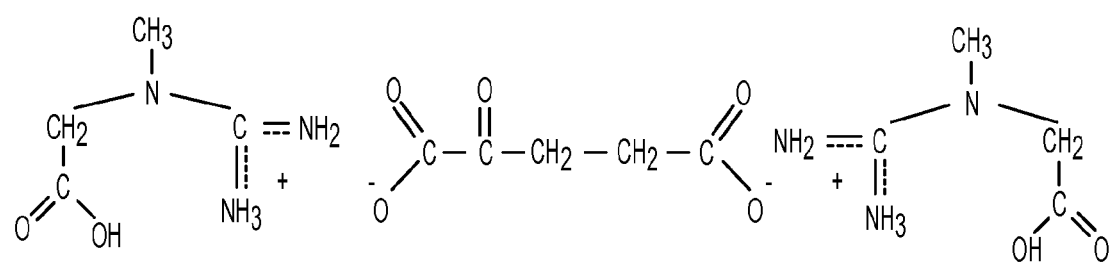
FIG. 1 is a schematic depiction of the ionic bonds and molecular arrangement of the creatine-α-Ketoglutarate product of the invention.

Herein, the terms "product" "composition" and "complex" are sometimes used interchangeably. "Product" means to emphasize that the invention is not limited by the particular structure the product has acquired. In other words, the invention is not limited by any concept as to the molecular arrangement of the bonded complex, the product is understood to have been created by ionic bonding and is expected to have a molecular arrangement as depicted in FIG. 1. "Complex" or composition" mean to emphasize the enhanced absorbability quality of the product.

The method of the invention is designed to provide an ionic-bonded complex comprising creatine and α-ketoglutarate at a molar ratio of about 2:1. The precise molar ratio or weight of the starting ingredients is not critical, as long as a molar ratio of about 2:1 creatine monohydrate and α-ketoglutarate is achieved. Starting quantities of creatine monohydrate and α-ketoglutarate may preferably be at a ratio of between about 2 to 2.3, more preferably between about 2.1 to 2.25. See a preferred embodiment of the starting ingredients and quantities presented in Table 1 (An Exemplary Preparation).

In addition, for effective creation of the ionic bonded product, sufficient calcium carbonate is provided to insure the desired pH is achieved and it is maintained throughout the procedure. A pH between about 5.8 to 7.4 for the mixture is desirable. A pH of about 6.8 is preferred. The pH is monitored by any standard means, e.g. with electronic micro-device. It should be noted that other pH stabilizing agents might replace the calcium carbonate.

All ingredients are in powder form and reasonable steps are taken to provide and maintain them dry and as free as possible of extra liquids beside liquid inherently present in the ingredients (water content of creatine monohydrate is approximately 12% to 15%, w/w). The vendor source is not critical, as long as the raw materials are dry, un-oxidized and of "A"-grade chemical purity. For example, the reagents are typically purchased from Sigma-Aldridge or Medisca, US.

The ingredients are dispensed and mixed/blended into the thermo-stable thick-wall glass reactor. The reactor is mounted over a high-shier electrical motor, which allows carry out mixing the ingredients at speeds of about 200-300 rpm and micronizing the particles at about 1000 rpm.

Table 1 provides typical starting quantities for a preparation that will produce just under 100 gr. of the stable product. The pH is adjusted by the addition of calcium carbonate in an empirically determined amount. For an exemplary preparation as described in Table 1, in order to achieve the desired pH and to maintain that pH in this range throughout the procedure, up to about 6.0 g (i.e. up to about 0.5 M), more preferably between about 3.0 g and 6.0 g and, more preferably yet, about 5.0 g of calcium carbonate are added.

TABLE 1

An Exemplary Preparation

| Compound | Molecular Weight | Starting Quantities for an Exemplary Preparation | Starting Molar Quantities per 100 g Composition |
| --- | --- | --- | --- |
| Creatine monohydrate | 145.15 | 40-45 g | 2.7-3.1* |
| α-Ketoglutarate | 146.11 | 20 g | 1.37* |
| Calcium carbonate | 100.09 | Up to about 5 g | 0.03 to 0.06 |
| l-Arginine | 174.2 | 15 g | 0.85 |
| l-Taurine | 125.15 | 15 g | 1.2 |
| l-Citrulline | 175.19 | 1.5 g | 0.285 |

*In the final product, these molecules are ionic bonded. Another way to consider this data is that the creatine and α-ketoglutarate in the final conjugate, upon ionic bonding, the relative molar ration is about 2 to 1.

Next, subjection to a series of intermittent electro-magnetic dischargers in the field of a magnetrone, under continuous stirring, takes place to create ionic bonding between the molecules present in the reactor. The ionization reaction occurs at about 61° C.

The concept is to allow the electromagnetic energy to ionize the ingredients and to produce the required bonding. The process is also optimized to eliminate any water vapors produced, but to keep the process short and at optimal temperature and duration, to prevent a possible accumulation of any superoxide by-products. Accordingly, the actual periods of times or numbers of cycles employed may differ, but it is important that the reaction reaches about 61° C. and that it does not noticeably start to oxidize. Excess heating tends to lead to oxidation. The above regimen of cycles of electromagnetic field treatment and cooling is the preferred approach.

However, it is possible to provide a steady stream of electromagnetic energy for a short-pulse period of time, wherein the internal temperature stays between about above 50° C. and about 61° C. for sufficient exposure to produce the ionic bonded complex. For a preferred embodiment, the internal temperature reaches and stays stable at about 61° C. The optimization of the system for the above alternative approach or for adjustments in starting materials is accomplished by following two criteria: the product should not be significantly oxidized and the proportion of the bonded material to leftover starting ingredients should be minimal. Application of both of these criteria are described below.

For a quantity of starting ingredients as in the Exemplary Preparation of Table 1, a preferred regimen calls for three 30 seconds cycles of electromagnetic field treatment at 61° C. and cooling to about 41° C. The cooling can be accomplished in any manner that achieves the principles listed above, but it is conveniently done at room temperature, preferably in a blender, to allow for the simultaneously vigorous stirring. Although the blending can be done in a blender, it is convenient and possible to achieve the blending by other means, e.g. mechanical stirring. The stirring for blending and heat optimization of the whole of the starting materials may be at any speed reasonable for the described purpose given the quantities involved, but it is preferably at between about 200 and 500 rpm, more preferably at between about 200 and 250 rpm. The process is calibrated so that, while the certain heating is unavoidable, it should not result in significant oxidation of the material. When oxidized, the material starts turning yellowish, and the color change can be monitored by the naked eye.

For example, for a typical quantity of ingredients as in the Preparatory Example of Table 1 (about 65-70 grams at this point of the process outlined here, before milling and before addition of amino acid components), three energy bursts/cooling cycles are preferred. It is feasible to proportionately scale the quantities processed; changes in the total amount of ingredients processed require recalibration to insure the mixture becomes bonded (as tested/described below) and it has not oxidized significantly, i.e. no yellowish tint is visible to the naked eye.

The ionic bonded preparation is fine milled at room temperature. Standard milling procedures are employed. Preferably a high shear force, e.g. 1000 rpm, is used for about 1 minute. This may cause also a cooling of the reaction mixture. Preferably, the temperature of the conjugate during milling remains (or is maintained) somewhat elevated, between about 41° C. and 61° C.

Viewing a sample under a light contrast microscope monitors the success of the milling step. What is desired is a relatively uniformly sized product, fine grains of preferably, about 200 microns, and the absence of a yellow tint. For the same purpose particle size can be monitored with a NRI Spectra device.

The next step in the preparatory process serves as a clean-up step and a quality control test. In this step, the powder product is exposed to a positive electrical field creating an accumulation of un-reacted anionic (negatively charged) or cationic (positively charged) compounds at the positive and negative electrodes, respectively. The electrodes are adjusted to the outer surface of the high shier blender. The material accumulated at the poles is removed away from the end product remaining in the reaction vessel, wherein the remaining product comprises stable ionic-bonded creatine-α-Ketoglutarate product. The end product continues to be free of yellow tint and is of relatively uniform fine particles of on average 200 microns powder, as described above.

Most of the initially provided starting materials should have been bonded and relatively little material should now accumulate at the poles. If the material accumulated at the poles appears to be in an excessive quantity, it can be weighed. If more than about 12% by weight of the starting materials was present at the electrical poles (un-reacted), that is an indication that the procedure needs recalibration and the product of the particular batch should be discarded or at least analyzed for proper bonding configuration, as discussed below.

Figure 2:
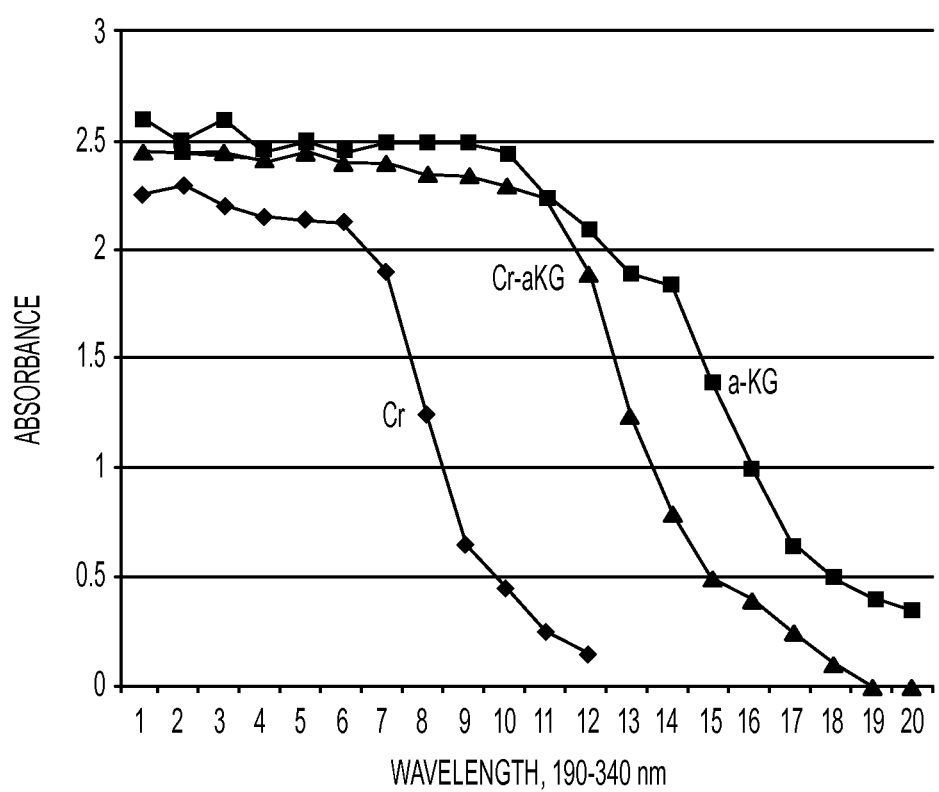
FIG. 2 depicts the distinct UV profiles of creatine; α-ketoglutarate; and creatine-α-Ketoglutarate product.

The creation of the conjugate can be monitored by spectral analysis. Relative to an untreated sample, the spectrum of the bonded molecule shows a peak located between the location of the peaks indicative of the creatine and the α-ketoglutaric acid peaks. FIG. 2 presents the UV absorbency spectra profiles of creatine monohydrate, alpha-ketoglutarate, and creatine α-Ketoglutarate, in aqueous solution. The relative position of the product in a spectral analysis is an indication that the desired product is produced. Likewise, spectral analysis is used also on the stored product, to assess its continued bonded state.

The creation of the conjugate, as well as its stability after storage, is also monitored and demonstrated by combining High Performance Liquid Chromatography with a Mass Spectra analysis (HPLC-MS). The HPLC column can be made of different sorbents. The sample is placed on a column with a suitable solvent, which in this case may be a polar solvent. The separation is in accordance to the interaction with the sorbent, the composition of the mobile/solvent phase, column dimensions and pressure applied. The exit peak is made up of a relatively clean/separated component of the mixture, its relative size indicates the amount of product and its exit time off the column is characteristic and reproducible when the separation is run under identical conditions. The peak/exit material is next analyzed by mass spec, which measures the mass to charge ratio of the material to identify its composition. The MS profile is also indicative of the presence of the conjugate of the invention.

Figure 3:
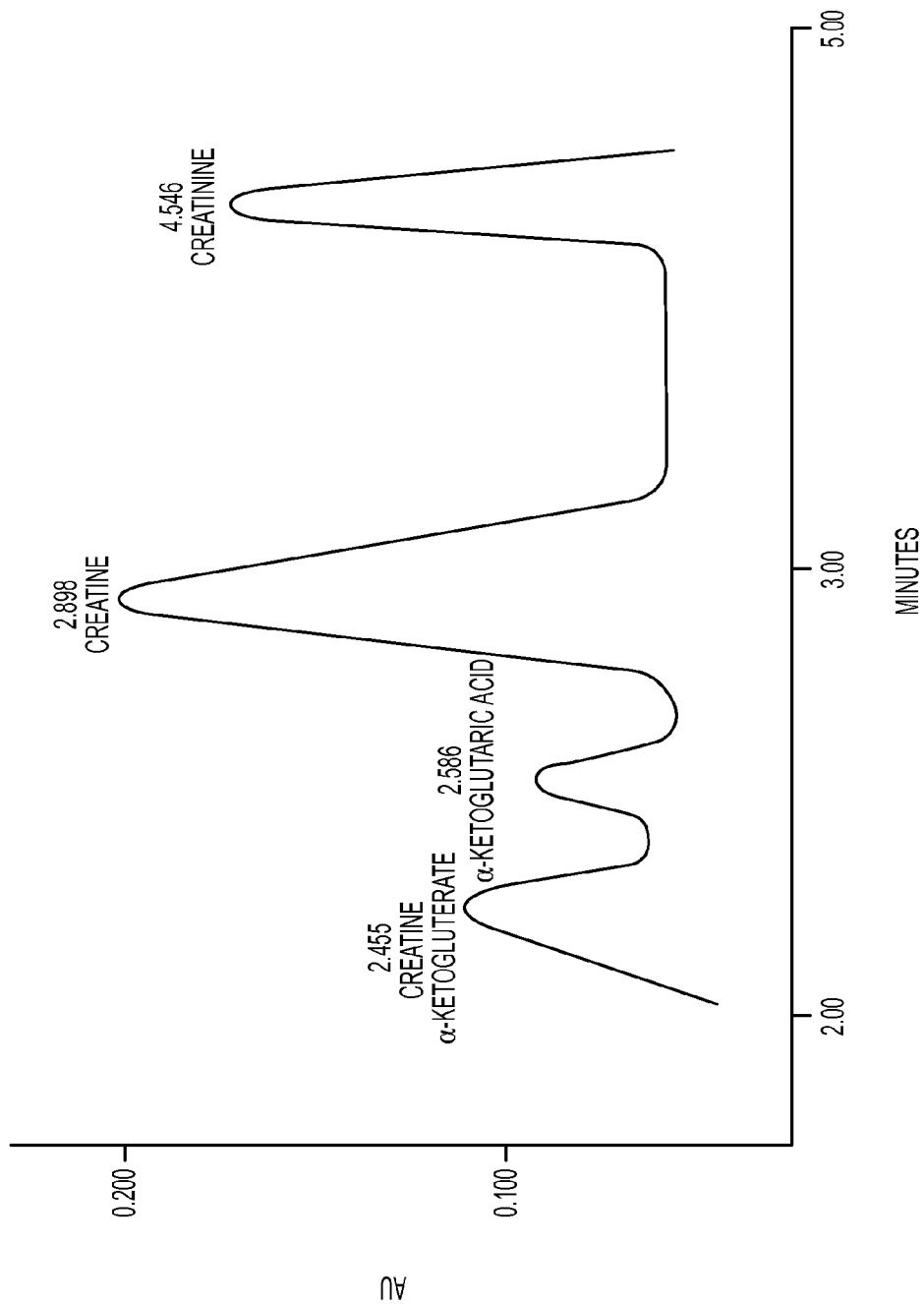
FIG. 3 depicts the HPLC-MS distinct spectral profiles of creatine; α-ketoglutarate; and creatine-α-Ketoglutarate product.

FIG. 3 presents a HPLC-MS analysis of a preparation as in Example 1. As shown, the creatine-α-ketoglutarate eluted in that system at past the two minute elution time.

NIR (near-infrared) spectroscopy was also occasionally used to characterize the chemical ID and yield of the end product in the ionic-boning series of reaction. NIR analysis is based on molecular overtone and combination vibrations. Such transitions are forbidden by the selection rules of quantum mechanics. As a result, the molar absorptivity in the near IR region is typically quite small. One advantage is that NIR can typically penetrate much farther into a sample than mid infrared radiation. Near-infrared spectroscopy is, therefore, not a particularly sensitive technique, but it can be very useful in probing bulk material with little or no sample preparation. The simple management often makes the NIR technique a method of choice as, in our case, for quick monitoring of the reaction outcome and checking the degree of uniformity of the final powder.

Figure 4:
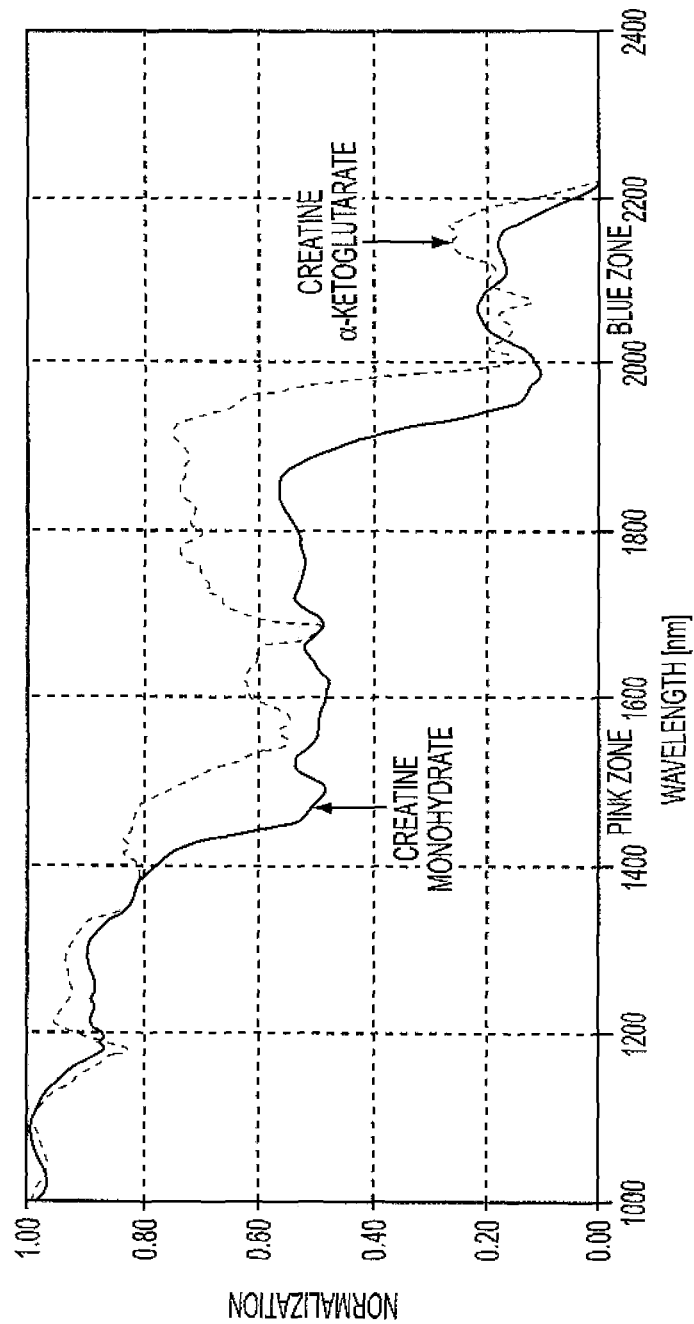
FIG. 4 depicts the Near Infrared (NIR) full chemical profile analysis of Creatine and α-Ketoglutarate.

FIG. 4 depicts a screen capture of the NIR Spectra full chemical analysis of a preparation as in Example 1. creatine nonohydrate and creatine α-Ketoglutarate have characteristically distinct NIR Spectra profiles: creatine-HOH—in the pink zone, and creatine α-Ketoglutarate—in the blue zone of the Spectra.

Optionally but desirably, at this point in the process, other supplements beneficial to energy and muscle mass production are added to the product. These supplements are added as dry powder and blended with the creatine α-ketoglutarate complex. Preferably, these supplements are added one-at-a-time, with blending. Most beneficially, three particular supplements are added, l-arginine, l-taurine and l-citrulline. More preferably yet, all three of these supplements are added. In a yet preferred embodiment, the final composition comprises up to about 12 parts of conjugated creatine α-ketoglutarate to about 3 parts l-arginine, 3 parts l-taurin and one part l-citrullin, by weight. For example, about 15 g of l-arginine and l-taurine each, and about 1.5 g of l-citrulline are added to the composition of ingredients in the Exemplary Preparation detailed in Table 1. In another optional step, the product after addition of the supplements is again fine milled.

The creatine α-ketoglutarate ionic bonded conjugate, supplemented with the amino acids, or not, may be dispensed into aliquots that allow facile distribution to the consumer of recommended dosages. The individual dosages are packaged in any reasonable container, but in particular, packers B630, color amber, size 150 cc, material PS, neck finish 45-400, height 3.815", diameter 2.251. Alternatively, the powder is sold in powder form in containers having multiple doses and comprising a total of from about 20 g to 200 g of the powder product. Multiple doses (individually packed or part of bulk powder) are packed in a container for distribution in commerce. This distribution container has, preferably, desiccating material included therein. For example a silica sleeve is provided. Any reasonably adequate materials are appropriate for the above storage of individual doses or retail container. However, it is preferred that the product of the invention be stored in a manner that allows it to remain dry and at room temperature and protected from light.

The creatine is better solublized when ionized as inionic bonded creatine α-Ketoglutarate and also provides better delivery of the creatine within biological systems, e.g. a human, than other known creatine supplements. Accordingly, an effective dose range for the creatine α-ketoglutarate ionic bonded with or without supplements, is relatively low. (If further supplemented with the amino acids, the conjugate and the supplements are sometimes referred to as "Torque-Power".) More preferably, the dosage does not exceed about 2 g of the formula per day, however it may vary within about the 1 g to 2 g range, depending on the stage of a training program an athlete might be undertaking and considerations such as age, gender, physical activity. More preferably, an individual dosage is about 2 g.

The container may include a scoop made of inert material for dispensing, literature suggesting a regimen/schedule of ingestion and other advice. Preferably, an individual dose may be placed sublingually and taken with a small amount of honey. Preferably, for a person at rest (on a non-training day), the dosage is ingested just before a meal (within about 10 minutes of meal time). For a person training it might be desirable that the ingestion takes place right before or immediately after a workout.

When kept at room temperature in dry and limited light conditions, the product in a stable form had a shelf-life of at least about 1 year. The condition of the stored material was assessed by its looks by eye and/or under the microscope (coloring, clumping) and smell. It also retained the bonded structure, as revealed by spectral analysis.

Example 1

A Bench-Top TorquePower Preparation

In one embodiment of the present invention, the product is prepared as follows:

45 g of creatine monohydrate, mol. mass 132.3; 20 g of α-ketoglutarate, mol. mass 146.11; and 5.0 g of calcium carbonate, mol. mass 100.0869 are dispensed and blended in a thermo stable glass beaker. They were treated in a domestic sized/powered microwave for 30 seconds and moved promptly to room temperature for mixing with a spatula for thirty seconds. The treating/stirring at room temperature cycle was repeated twice more, with essentially no time breaks between the cycles.

The material placed in the center of a pre-prepared plate with means for applying constant electric current over the plate. 110 volts were applied for 2 minutes. Residue was observed to have accumulated at the poles. The cumulative residue was removed and it weighed just under 3 g. Samples were taken and the samples later allowed the UV and the HPLC-MS analysis, or NIR spectra screening of, respectively, FIGS. 2, 3, and 4 and provided data as shown in these figures.

Standard milling was applied to the still warm conjugate. Microscopic analysis revealed a uniform powder was produced.

L-arginine (15 g), l-taurin (15 g) and l-citrulline (1.5 g) were added, sequentially with of stifling at 250 rpm.

The process resulted in the preparation of a product we refer to as TorquePower, which was white in appearance, uniform in crystal size and where about 60% of the product is an ionic bonded creatine α-ketoglutarate and the reminder of the product consists of blended-in supplements.

Example 2

Additional Creatine is Delivered Rapidly after Ingestion of the Conjugate

The estimated total body pool of total creatine in a 158 lbs (70 kg) man is about 120 g. See: Elevation of creatine in resting and exercised muscle of normal subjects by creatine supplementation 1992. Clin. Sci; 83: 367-74. Based on measurements of renal excretion of creatinine (Crn), the daily requirement for creatine from endogenous biosynthesis, is approximately 2 g/day, or 340 μmol/kg/day. This suggests a relatively slow turnover rate of creatine in skeletal muscle with a T½ of approximately 26 days. See: Scientific facts behind creatine monohydrate as sport nutrition supplement 1999. J. Sports Med. Phys. Fitness; 39 (3): 179-88.

Our interest in α-ketoglutarate was mostly because of its remarkably high chemical affinity to the nitrogen of the guanidinoacetate group of creatine. We were able to exploit this property of α-ketoglutarate to bioengineer an ionic-bonded creatine α-ketoglutarate delivering vehicle for creatine and be able to deliver above creatine at a level above that the level normally encountered by the body. Chemical analysis of clinical samples support the fact that increased creatine was available within a short time period after sublingual ingestion, after about ten minutes. Essentially twice of the normal level secreted is observed.

Example 3

Peak Performance of Athletes is Observed Much Quicker when the Product of the Invention is Provided Repeated observations were made of the length of time after delivery of the product of the invention and other creatine supplements. The other supplements which were compared comprised creatine by itself and a covalently bonded creatine α-ketoglutarate preparation, containing which was produced by wet chemistry, resulting in a 2:1 molar ratio of creatine to α-ketoglutarate. To more clearly distinguish the products, the product of the invention was provided at about half the dose provided from other preparations. (The actual dose depended on the athlete.)

Most notably was the time required for the supplement to become effective. The product of the invention produced peak performance within as little as ten minutes after delivery. The other supplements required from 2-8 hrs before full benefits were seen.

The performance evaluations were made by experienced coaches, overlooking standard athletic tasks.

Example 4

Creatine and Athletic Performance

A pilot trial was designed to find out the effects of Torque-Power effect in young adult advanced weight lifters is true. Ten male weight lifters and five female cross-Fit athletes of age 23.0±5.0 years volunteered in the 10 day long trial. During this period of time athletes were instructed to consume daily a diet comprising 2 g/kg BM animal protein and a 1:1 protein/carbohydrate (CHO) ratio. All athletes participated in daily short duration (30-35 min) high intensity (PRmax 180 bpm) workouts. Immediately after each workout, athletes received Torque Power Formula, 2 scoops with honey sublingually. Athletes were recommended not to take any OTK medicines and drink water ad libidum. A day before athletes have been asked to fulfill a set of power exercise with 1RM: vertical jump from spot, box-jump, squat, bench press, cleans, midsection skin grid. The same clip of exercise, 1RM athletes executed next day after the trial was over. Results of the trial are summarized in Table 2.

TABLE 2

| Performance Improvement | |
|---|---|
| Exercise | Performance Improvement, % |
| Vertical jump | 14.0 |
| Box-jump | 7.0 |
| Squat | 25.0 |
| Bench press | 23.0 |
| Cleans | 17.0 |
| Skin grid, midsection | −2.7 |

The invention described above should be read in conjunction with the accompanying claims and drawings. The description of embodiments and examples enable one to practice various implementations of the invention and they are not intended to limit the invention to the preferred embodiment, but to serve as a particular example of the invention. Those skilled in the art will appreciate that they may readily use the conception and specific embodiments disclosed as a basis for modifying or designing other methods and systems for carrying out the same purposes of the present invention.

All references, including publications, patent applications, patents, and website content cited herein are hereby incorporated by reference to the same extent as if each reference were individually and specifically indicated to be incorporated by reference and was set forth in its entirety herein.

The use of the terms "a" and "an" and "the" and similar referents in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A method of preparing a dry, non-oxidized, stable complex of creatine and α-ketoglutarate product with enhanced stability and absorbability, comprising:
   in a thermo-stable reactor, provide in powder form, creatine monohydrate and α-ketoglutarate and a compound to allow the adjusting and maintaining the pH at between about 5.8 to 7 (together a mixture);
   stir and blend; and
   provide electromagnetic energy, whereby the internal temperature of about 61° C. for a period of time sufficient to allow an ionic-bonding of the creatine and alpha-ketoglutarate,
   wherein the product is at a molar ratio of 2:1 of creatine: alpha-ketoglutarate, and
   the product is dry, non-oxidized, stable.

2. The method of claim 1, wherein said step to provide electromagnetic energy optionally comprises cycles of short bursts of energy followed by short cooling periods.

3. The method of claim 2, wherein said cooling is accompanied by blending the ingredients to allow more rapid cooling and to release water vapors from the mixture.

4. The method of claim 1, wherein, the compound added to control the pH is calcium carbonate, at between about 0.03 M and about 0.06 M.

5. The method of claim 1, wherein the pH is maintained at about 6.8.

6. The method of claim 1, wherein the products after the bonding process is finished are fine milled.

7. The method of claim 6, wherein the products undergoing milling are maintained at about room temperature.

8. The method of claim 1, wherein after the milling, the powder product is exposed to a constant electrical field creating an accumulation of unreacted ionic or cationic compounds at the positive and negative electrode, respectively, and the material accumulated at the poles is removed away from the end product remaining in the mixing reactor, wherein the remaining product comprises a stably bonded creatine and α-ketoglutarate.

9. The method of claim 8, wherein said step of exposure to a constant electric field precedes the milling step.

10. The method of claim 1, followed by the addition of at least one from among l-arginine; l-taurine; and citrulline are added and blended with the creatine-α-ketoglutarate product.

11. The method of claim 10, wherein the amount of ingredients comprises about 40-45 grams creatine monohydrate; about 20 grams α-ketoglutarate; from about 2 to about 6 grams calcium carbonate, about 15 grams of l-arginine; about 15 grams of l-taurine; and about 1.5 grams of l-citrulline.

12. The method of claim 11, wherein the amount of calcium carbonate is about 5 grams.

13. The method of claim 11, wherein the amount of ingredients are scaled-up, while preserving the relative ratio of the ingredients.

14. The method of claim 10, wherein the resulting creatine α-ketoglutarate product is next stored in a reduced humidity environment until ingestion by a patient.

15. A creatine α-ketoglutarate product made by the method of claim 1.

16. A creatine α-ketoglutarate product made by the method of claim 10.

17. The creatine α-ketoglutarate product made by the method of claim 8, wherein, after the removal of un-reacted compounds, the creatine is present to at least about 55%, 65%, 70%, 75%, 80%, 85%, 90%, or 95% as an ionic-bonded product with α-ketoglutarate.

18. A kit for delivering to a mammal individual dosages of an end-product made by the method of claim 7, comprising creatine α-ketoglutarate ionic-bonded product and instructions for oral ingestion of the product, as opposed to swallowing the powders.

19. The method of claim 1, wherein the creatine and alpha-ketoglutarate ingredients are provided at a ratio of from about 2 to 2.4 moles of creatine monohydrate to about 1 mole of alpha-ketoglutarate.

20. The method of claim 19, wherein the creatine monohydrate and alpha-ketoglutarate ingredients are provided at a molar ratio of about 2.25:1.

21. A kit for delivering to a mammal individual dosages of an end-product made by the method of claim 10, comprising creatine α-ketoglutarate ionic-bonded product and instructions for oral ingestion of the product, as opposed to swallowing the powders.

* * * * *